US005561151A

United States Patent [19]
Young et al.

[11] Patent Number: 5,561,151
[45] Date of Patent: Oct. 1, 1996

[54] ANTIPYRETIC AND ANALGESIC METHODS OF USING OPTICALLY PURE R-ETODOLAC

[75] Inventors: James W. Young, Palo Alto, Calif.; Nancy M. Gray, Marlborough, Mass.; William J. Wechter, Redlands, Calif.

[73] Assignee: Sepracor Inc., Marlborough, Mass.

[21] Appl. No.: 368,735

[22] Filed: Jan. 4, 1995

Related U.S. Application Data

[63] Continuation of Ser. No. 29,834, Mar. 11, 1993, abandoned, which is a continuation-in-part of Ser. No. 853,222, Mar. 13, 1992, abandoned.

[51] Int. Cl.$^6$ ........................................... A61K 31/40
[52] U.S. Cl. ............................................ 514/411
[58] Field of Search .................................. 514/411

[56] References Cited

U.S. PATENT DOCUMENTS

| | | | |
|---|---|---|---|
| 3,843,681 | 10/1974 | Demerson et al. | 260/326.14 |
| 3,896,145 | 7/1975 | Berger et al. | 260/315 |
| 3,904,682 | 9/1975 | Fried et al. | 260/520 |
| 4,501,899 | 2/1985 | Abraham et al. | 548/432 |
| 4,515,961 | 5/1985 | Demerson et al. | 548/432 |
| 4,520,203 | 5/1985 | Abraham et al. | 548/432 |
| 4,927,854 | 5/1990 | Sunshine et al. | 514/570 |
| 4,962,124 | 10/1990 | Sunshine et al. | 514/568 |
| 4,983,765 | 1/1991 | Lukas et al. | 562/401 |

FOREIGN PATENT DOCUMENTS

| | | | |
|---|---|---|---|
| 1316312 | 5/1973 | United Kingdom | C07D 27/48 |
| 1331505 | 9/1973 | United Kingdom | C07D 63/12 |

OTHER PUBLICATIONS

Brune et al., "Aspirin–like drugs may block pain independently of prostaglandin synthesis inhibition", *Experientia* 47:257–261 (1991).

Brocks and Jamali, "The pharmacokinetics of etodolac enantiomers in the rat", *Drug Metabolism and Disposition* 18(4): 471–475 (1990).

Geisslinger et al., "Pharmacokinetics of S(+)–and R(–)–ibuprofen in volunteers and first clinical experience of S(+)–ibuprofen in rheumatoid arthritis", *Eur. J. Clin. Phar.* 38(5): 493–497 (1990).

Knihinicki et al., "Stereoselective disposition of ibuprofen and flurbiprofen in rats", *Chirality* 2: 134–140 (1990).

Muller et al., "Pharmacological aspects of chiral nonsteroidal anti–inflammatory drugs", *Fundam. Clin. Pharmacol.* 4: 617–634 (1990).

Murray and Brater, "Nonsteroidal anti–inflammatory drugs", *Clin. Pharm.* 6(2): 365–397 (1990).

Williams, "Enantiomers in arthritic disorders", *Pharmac. Ther.* 46: 273–295 (1990).

Jamali et al., "Enantioselective aspects of drug action and disposition: Therapeutic pitfalls", *J. Pharm. Sci.* 78(9): 696–715 (1989).

Caldwell et al., "The metabolic chiral inversion and dispositional enantioselectivity of the 2–arylpropionic acids and their biological consequences", *Biochemical Pharmacology* 37(1): 105–114 (1988).

Jamali, "Research methodology in NSAID monitoring: Plasma concentrations of chiral drugs", *J. Rheum.* 15: 71–74 (1988).

Jamali et al., "Application of a stereospecific high–performance liquid chromatography assay to a pharmacokinetic study of etodolac enantiomers in humans", *J. Pharm. Sci.* 77(11): 963–966 (1988).

Jamali, "Pharmacokinetics of enantiomers of chiral non–steroidal anti–inflammatory drugs", *Eur. J. Drug Met. Pharm.* 13(1): 1–9 (1988).

Williams and Day, "The contribution of enantiomers to variability in response to anti–inflammatory drugs", *Anti–Rheumatic Drugs* AAS 24: 76–84 (1988).

Humber, "Etodolac: The chemistry, pharmacology, metabolic disposition, and clinical profile of a novel anti–inflammatory pyranocarboxylic acid", *Medicinal Research Reviews* 7(1): 1–28 (1987).

Yamaguchi et al., "The inhibitory activities of 480156–S and its related compounds on prostaglandin synthetase", *Folia pharmacol. japon.* 90: 295–302 (1987) (contains English abstract).

Humber et al., "Etodolac (1,8–diethyl–1,3,4,9–tetrahydropyrano[3,4–b]–indole–1–acetic acid): A potent antiinflammatory drug. Conformation and absolute configuration of its active enantiomer", *J. Med. Chem.* 29: 871–874 (1986).

Meffin et al., "Enantioselective disposition of 2–arylpropionic acid nonsteroidal anti–inflammatory drugs. I. 2–phenylpropionic acid disposition", *J. Pharm. Exp. Therm.* 238(1): 280–287 (1986).

Singh et al., "Stereoselective gas chromatographic analysis of etodolac enantiomers in human plasma and urine", *J. Chromat.* 382: 331–337 (1986).

Singh et al., "Pharmacokinetics of the enantiomers of tiaprofenic acid in humans", *J. Pharm. Sci.* 75(5): 439–442 (1986).

Williams and Day, "Stereoselective disposition—basis for variability in response to NSAID's", *Non–steroidal Anti–Inflammatory Drugs* 17: 119–126 (1985).

Scrip's New Product Review No. 4 Etodolac, PJB Publications Ltd. (1985).

(List continued on next page.)

*Primary Examiner*—Marianne M. Cintins
*Assistant Examiner*—William R. A. Jarvis
*Attorney, Agent, or Firm*—Pennie & Edmonds

[57] ABSTRACT

Methods are disclosed utilizing optically pure R(–) etodolac for the treatment of pain, including but not limited to pain associated with toothaches, headaches, sprains, joint pain and surgical pain, for example dental pain and ophthalmic pain, while substantially reducing adverse effects which are associated with the administration of the racemic mixture of etodolac. The optically pure R(–) etodolac is also useful in treating pyrexia while substantially reducing the adverse effects associated with the administration of the racemic mixture of etodolac.

16 Claims, No Drawings

OTHER PUBLICATIONS

Hutt and Caldwell, "The importance of stereochemistry in the clinical pharmacokinetics of the 2-arylpropionic acid non-steroidal anti-inflammatory drugs", *Clinical Pharmacokinetics* 9: 371–373 (1984).

Tamassia et al., "Pharmacokinetics of the enantiomers of indoprofen in man", *Int. J. Clin. Pharm. Res.* IV(3): 223–230 (1984).

Demerson et al., "Resolution of etodolac and antiinflammatory and prostaglandin synthetase inhibiting properties of the enantiomers", *J. Med. Chem.* 26: 1778–1780 (1983).

Hutt and Caldwell, "The metabolic chiral inversion of 2-arylpropionic acids—a novel route with pharmacological consequences", *J. Pharm. Pharmacol.* 35: 693–704 (1983).

Goto et al., "Separation and determination of naproxen enantiomers in serum by high-performance liquid chromatography", *J. Chromat.* 239: 559–564 (1982).

Kemmerer et al., "Stereospecific assay and stereospecific disposition of racemic carprofen in rats", *J. Pharm. Sci.* 68(10): 1274–1280 (1979).

Inoue et al., *Chemical Abstracts*, vol. 114, No. 25, abstract No. 240197k, 1991.

Brocks et al., *Biological Abstracts*, vol. 93, No. 4, abstract # 44336, 1991.

ANTIPYRETIC AND ANALGESIC METHODS OF USING OPTICALLY PURE R-ETODOLAC

This is a continuation of application Ser. No. 08/029,834 filed Mar. 11, 1993, now abandoned, which is a continuation-in-part of application Ser. No. 07/853,222 filed Mar. 13, 1992, now abandoned, each of which is incorporated by reference herein in its entirety.

BACKGROUND OF THE INVENTION

This invention relates to novel compositions of matter containing optically pure R-etodolac. These compositions possess potent activity in treating pain including, but not limited to, pain associated with toothaches, headaches, sprains, joint pain and surgical pain, for example dental pain and ophthalmic pain, while substantially reducing adverse effects associated with the administration of the racemic mixture of etodolac including but not limited to gastrointestinal, renal and hepatic toxicities, as well as leukopenia. Additionally, these novel compositions of matter containing optically pure R-etodolac are useful in treating or preventing pyrexia while substantially reducing the adverse effects associated with the administration of the racemic mixture of etodolac. Also disclosed are methods for treating the above-described conditions in a human while substantially reducing the adverse effects that are associated with the racemic mixture of etodolac, by administering the R-isomer of etodolac to said human.

The active compound of the present compositions and methods is an optical isomer of the compound etodolac, also known as etodolic acid, which is described in Humber, L. G. et al., *J. Med. Chem.* 29: 871–874 (1986); Humber, L. G. *Medicinal Research Reviews* 7(1): 1–28 (1987); and U.S. Pat. No. 3,843,681 and German Patent No. DE 2,226,340, both to Demerson et al. Chemically, this R-isomer is (−) 1,8-diethyl-1,3,4,9-tetrahydropyrano-[3,4-b]indole-1-acetic acid. This isomer will hereinafter be referred to as R(−) etodolac. This term also includes the substantially optically pure and optically pure R(−) etodolac isomer.

Etodolac, which is the subject of the present invention, is available commercially only as the 1:1 racemic mixture. That is, it is available only as a mixture of optical isomers, called enantiomers. The racemic mixture of etodolac is commercially available under the trade names ULTRADOL® and LODINE® by Ayerst Laboratories, New York.

1.1. Steric Relationship and Drug Action

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of the beta-adrenergic blocking agent, propranolol, which is known to be 100 times more potent than the D-enantiomer.

Furthermore, optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer has been believed to be a potent teratogen.

1.2. Pharmacological Profile

Etodolac is a member of a class of compounds known as nonsteroidal anti-inflammatory drugs (NSAIDs). As a class of agents, NSAIDs exhibit analgesic, anti-inflammatory, and antipyretic activity. The class includes well known commercial pain relievers such as ibuprofen and aspirin.

It should be noted that etodolac does not possess the 2-arylpropionic acid structure which is common to many NSAIDs, although it has been classified as belonging to this group of compounds. See Stecher, V. J. "Anti-Inflammatory Drugs" p. 137–147 in *Handbook of Stereoisomers: Therapeutic Drugs*, ed. Donald F. Smith, CRC Press, Inc., Boca Raton, Fla. 1989. Due to the fixed nature of etodolac's asymmetric carbon, it is not expected to undergo chiral inversion. Jamali, F., *Eur. J. Drug Met. and Pharmacokin.* 13(1): 1–9 (1988).

Etodolac, a member of the pyranocarboxylic acid class of NSAIDs, is capable of treating a variety of pain states and inflammatory conditions, and it apparently has the potential to alter the progression of skeletal changes in rheumatoid arthritis. This profile is presumably the consequence of the peripheral pharmacologic activity of etodolac as a cyclooxygenase enzyme inhibitor capable of the inhibition of prostaglandin synthesis with possible consequent effects on bradykinin or other mediators. Etodolac, unlike the opioids, has no addictive potential or risk of physical dependency.

Etodolac has not been reported to induce respiratory depression, significant cardiovascular effects, or psychomotor effects—effects that are somewhat characteristic of the opiates. Rather, the pharmacology of etodolac appears to be linked to its effect on the cyclooxygenase enzyme system, with only a very weak inhibitory effect on both the 5-lipoxygenase and 12-lipoxygenase pathways of arachidonic acid metabolism. Sirois, P. et al., *Inflammation* 8: 353–364 (1984).

Prostaglandins are synthesized from long chain unsaturated fatty acids, principally arachidonic acid, which is first liberated by hydrolysis from cell membrane phospholipids through the action of phospholipases. Arachidonic acid is then converted by a cyclooxygenase enzyme to prostaglandin endoperoxide $G_2$, then to prostaglandin $H_2$, and to other products including the more stable prostaglandins of the E and F series. Inhibition of the cyclooxygenase enzyme with NSAIDs, such as acetylsalicylic acid, ibuprofen, zomepirac, and etodolac, prevents the formation of thromboxane $A_2$ and all of the prostaglandins. The stable and unstable prostaglandins participate either directly or indirectly in a broad variety of cell or tissue processes, including presumably the aforementioned conditions, smooth muscle contraction and relaxation, platelet aggregation, some cell secretion, and possibly other metabolic processes. See, e.g., Mustard, J. F., *Acetylsalicylic Acid: New Uses for an Old Drug*, eds. Barnett, Hirsh, and Mustard, Raven Press, New York, pp. 1–15 (1982). Thus, inhibition of prostaglandin synthesis explains much of the pharmacology of etodolac and related drugs.

Etodolac has been shown to be a potent structurally novel anti-inflammatory agent with analgesic activity, at least as effective as other NSAIDs. The compound has been resolved through chromatographic separation of its diastereoisomeric esters. The enantiomers have been studied in vitro for their effect on prostaglandin synthetase, and for their effect on adjuvant-induced arthritis in rats. Both biochemical and pharmacological results suggest that nearly all of the effects of etodolac are due to the (+) enantiomer. Demerson, C. A. et al., *J. Med. Chem.* 26: 1778–1780 (1983). This active (+) enantiomer of etodolac has been assigned an S absolute configuration on the basis of crystallographic analysis. Humber, L. G. et al., *J. Med. Chem.* 29: 871–874. (1986).

However, the R isomer of etodolac has been suggested to be the active enantiomer of the compound in one reference. See Williams, K. M., *Pharmac. Ther.* 46: 273–295 (1990). A review of this reference indicates that this suggestion is likely in error. Williams cites the above-mentioned references by Humber et al. (1986) and Demerson et al. (1983) to demonstrate which isomer of etodolac is active. A review of those references clearly indicates that the S(+) isomer is the active compound.

The racemic mixture of etodolac has been demonstrated both preclinically and clinically to reverse skeletal changes associated with adjuvant arthritis in rats, and to retard progression of osseous defects in patients with active rheumatoid arthritis. Humber, L. G. et al., *J. Med. Chem.* 29: 871–874 (1986); Humber, L. G., *Medicinal Research Reviews* 7(1): 1–28 (1987); Zvaifler, N., *Clin. Rheumatology* 8(1): 43–53 (1989); Ryder, S. et al., *Current Therapeutic Research* 33(6): 948–964 (1983).

Pharmacokinetic studies in the rat suggest no in vivo inversion of the enantiomers of etodolac. See Jamali et al., *J. Liquid Chromatogr.*, 12(10): 1835–1850 (1989). The pharmacokinetic profiles of the enantiomers of etodolac in man indicate that the S-enantiomer may be more rapidly excreted or metabolized than the R-enantiomer. See Mroszczak et al., *Clin. Pharmacol. Ther.*, PI-13, p.126 (February 1991).

Pain is a common symptom, reflecting either physical (i.e., the result of tissue injury or inflammation) or emotional discomfort. Pain is a complex subjective phenomenon comprised of a sensation reflecting real or potential tissue damage, and the affective response this generates. Pain may be classified as either acute or chronic, and it is of a variety of particular types. Acute pain is an essential biologic signal of the potential for, or the extent of, tissue injury. In contrast, chronic pain is physically and psychologically debilitating, and it no longer serves its adaptive biologic role. In many patients, organic disease may be insufficient to explain the degree of pain. Chronic pain may be associated with conditions including but not limited to osteoarthritis, rheumatoid arthritis, soft tissue pain syndromes, and headaches.

Pyrexia, or fever, is an elevation in body temperature as a result of infection, tissue damage, inflammation, graft rejection, malignancy or other disease states. The regulation of body temperature requires a delicate balance between the production and loss of heat. The hypothalamus regulates the target point at which body temperature is maintained. In fever, this target point is elevated; antipyretic compositions promote its return to a normal level.

Many of the NSAIDs cause somewhat similar adverse effects. These adverse effects include but are not limited to gastrointestinal, renal and hepatic toxicities. The administration of the racemic mixture of etodolac has been found to cause these toxicities, as well as other adverse effects. These other adverse effects include but are not limited to nausea, somnolence, headache, dizziness, pruritis, increased sweating, increases in bleeding times due to disruption of platelet function (e.g., thrombocytopenia), and prolongation of gestation due to uterine effects.

Further, leukopenia (decreased white cell count in the blood) is a known side effect of NSAIDs. Agranulocytosis is an acute disease caused by a precipitous drop in the number of white blood cells. The leukopenia/agranulocytosis syndrome has been described for several NSAIDs, such as indomethacin, ketoprofen, and ibuprofen. Indeed, such NSAIDs are contraindicated in patients whose immune systems are compromised by HIV infection, chemotherapy, ionizing irradiation, corticosteroids, immunosuppressives, etc. or by such conditions as emphysema, bronchiectasis, diabetes mellitus, leukemia, burns and the like. Although the overall incidence is low, agranulocytosis is a life-threatening syndrome that develops very rapidly. Periodic white-cell counts are therefore of little help in providing early warning of this syndrome.

Thus, it would be particularly desirable to find a compound with the advantages of the racemic mixture of etodolac which would not have the aforementioned disadvantages.

SUMMARY OF THE INVENTION

It has now been discovered that the optically pure R-isomer of etodolac is a potent analgesic that substantially reduces adverse effects which are associated with the administration of the racemic mixture of etodolac, including but not limited to gastrointestinal, renal and hepatic toxicities, increases in bleeding times, leukopenia, and prolongation of gestation. The present invention is also based in part on the discovery that these novel compositions of matter containing the optically pure R-isomer of etodolac are useful in treating or preventing pyrexia while substantially reducing the above-described adverse effects associated with the administration of racemic etodolac. The present invention also includes methods for treating the above-described conditions in a human while substantially reducing the adverse effects that are associated with the racemic mixture of etodolac, by administering the optically pure R-isomer of etodolac to said human.

DETAILED DESCRIPTION OF THE INVENTION

The present invention encompasses a method of eliciting an analgesic effect in a human which comprises administering to a human in need of analgesic therapy an amount of R-etodolac or a pharmaceutically acceptable salt thereof, substantially free of its S(+) stereoisomer, said amount being sufficient to alleviate pain.

Further, the present invention encompasses a method of eliciting an analgesic effect in a human, while substantially reducing the concomitant liability of adverse effects associated with the administration of racemic etodolac, which comprises administering to a human in need of analgesic therapy, an amount of R-etodolac, or a pharmaceutically acceptable salt thereof, substantially free of its S(+) stereoisomer, said amount being sufficient to alleviate pain, but insufficient to cause the adverse effects associated with the administration of the racemic mixture of etodolac.

The present invention encompasses an analgesic composition for the treatment of a human in need of analgesic therapy, comprising an amount of R-etodolac or a pharmaceutically acceptable salt thereof, substantially free of the S(+) stereoisomer.

The present invention also encompasses an analgesic composition for the treatment of a human in need of analgesic therapy, which comprises an amount of R-etodolac or a pharmaceutically acceptable salt thereof, substantially free of its S(+) stereoisomer, said amount being sufficient to alleviate pain but insufficient to cause the adverse effects associated with the racemic mixture.

The present invention encompasses a method of treating or preventing pyrexia in a human which comprises administering to a human an amount of R-etodolac or a pharmaceutically acceptable salt thereof, substantially free of its S(+) stereoisomer, said amount being sufficient to alleviate or prevent said pyrexia.

The present invention further encompasses a method of treating or preventing pyrexia in a human, while substantially reducing the concomitant liability of adverse effects associated with the administration of racemic etodolac, which comprises administering to a human in need of such therapy an amount of R-etodolac or a pharmaceutically acceptable salt thereof, substantially free of its S(+) stereoisomer, said amount being sufficient to alleviate or prevent said pyrexia but insufficient to cause adverse effects associated with the administration of the racemic mixture of etodolac.

Further, the present invention encompasses an antipyretic composition for the treatment of a human, comprising an amount of R(-) etodolac or a pharmaceutically acceptable salt thereof, substantially free of the S(+) stereoisomer.

In addition, the present invention encompasses an antipyretic composition for the treatment of a human in need of such therapy which comprises an amount of R-etodolac or a pharmaceutically acceptable salt thereof, substantially free of its S(+) stereoisomer, said amount being sufficient to alleviate or prevent pyrexia but insufficient to cause adverse effects associated with the administration of racemic etodolac.

The available racemic mixture of etodolac (i.e., a 1:1 mixture of the two enantiomers) possesses analgesic and antipyretic activity; however, this commercially available drug, while offering the expectation of efficacy, causes adverse effects. Utilizing the substantially optically pure R-isomer of etodolac results in clearer dose-related definitions of efficacy, diminished adverse effects, and accordingly, an improved therapeutic index. It is therefore more desirable to use the R-isomer of etodolac than the racemic mixture.

The term "adverse effects" includes, but is not limited to, gastrointestinal, renal and hepatic toxicities, leukopenia, nausea, somnolence, headache, dizziness, pruritis, increased sweating, increases in bleeding times due to, e.g., thrombocytopenia, and prolongation of gestation. The term "gastrointestinal toxicities" includes but is not limited to gastric and intestinal ulcerations and erosions. The term "enal toxicities" includes but is not limited to such conditions as papillary necrosis and chronic interstitial nephritis.

The term "substantially free of its S(+) stereoisomer" as used herein means that the compositions contain at least 90% by weight of R-etodolac and 10% by weight or less of S-etodolac. In a preferred embodiment the term "substantially free of the S(+) stereoisomer" means that the composition contains at least 99% by weight of R-etodolac and 1% or less of S-etodolac. In the most preferred embodiment, the term "substantially free of the S(+) stereoisomer" as used herein means that the composition contains greater than 99% by weight of R-etodolac and less than 1% of the corresponding S(+) etodolac. These percentages are based upon the total amount of etodolac present in the composition. The phrases "substantially optically pure R-isomer of etodolac" or "substantially optically pure R-etodolac" and "optically pure R-isomer of etodolac" or "optically pure R-etodolac" are also encompassed by the above-described amounts.

The term "eliciting an analgesic effect" as used herein means treating, relieving, ameliorating or preventing mild to moderate pain. For example, such pain includes but is not limited to pain associated with toothaches, headaches, sprains, joint pain, surgical pain, dental pain, and ophthalmic pain.

The term "pyrexia" as used herein means the elevation of body temperature brought about by infectious disease, tissue damage, inflammation, graft rejection, malignancy or other disease states.

The chemical synthesis of the racemic mixture of etodolac can be performed by the method described in Demerson et al., U.S. Pat. No. 3,843,681; and Demerson et al., *J. Med. Chem.* 19(3): 391–395 (1976), the disclosures of which are hereby incorporated by reference.

The R(-) isomer of etodolac may be obtained by resolution of the mixture of enantiomers of etodolac using conventional means such as the formation of a diastereomeric salt with a basic optically active resolving acid; see, for example "Stereochemistry of Carbon Compounds," by E. L. Eliel (McGraw Hill, 1962); Lochmuller, C. H. et al., *J. Chromatogr.* 113(3): 283–302 (1975); "Enantiomers, Racemates and Resolutions," by J. Jacques, A. Collet, and S. H. Wilen, (Wiley-Intenscience, New York, 1981); and S. H. Wilen, A. Collet, and J. Jacques, *Tetrahedron* 33: 2725 (1977).

The magnitude of a prophylactic or therapeutic dose of R-etodolac in the acute or chronic management of disease will vary with the severity of the condition to be treated, and the route of administration. The dose, and perhaps the dose frequency, will also vary according to the age, body weight, and response of the individual patient. In general, the total daily dose range for R-etodolac, for the conditions described herein, is from about 200 mg to about 2500 mg, in single or divided doses. Preferably, a daily dose range should be between about 200 mg to about 1000 mg, in single or divided doses. In managing the patient, the therapy should be initiated at a lower dose and increased depending on the patient's global response. It is further recommended that infants, children, patients over 65 years, and those with impaired renal or hepatic function initially receive lower doses, and that they be titrated based on global response and blood level. It may be necessary to use dosages outside these ranges in some cases. Further, it is noted that the clinician or treating physician will know how and when to interrupt, adjust or terminate therapy in conjunction with individual patient response. The terms "an amount sufficient to alleviate pain but insufficient to cause said adverse effects" and "an amount sufficient to alleviate or prevent said pyrexia but insufficient to cause said adverse effects" are encompassed by the above-described dosage amounts and dose frequency schedule.

Any suitable route of administration may be employed for providing the patient with an effective dosage of R-etodolac. For example, oral, rectal, parenteral (subcutaneous, intravenous, intramuscular), intrathecal, transdermal, and like forms of administration may be employed. Dosage forms include tablets, troches, dispersions, suspensions, solutions, capsules, patches, and the like.

The pharmaceutical compositions of the present invention comprise R-etodolac as the active ingredient, or a pharmaceutically acceptable salt thereof, and may also contain a pharmaceutically acceptable carrier, and optionally, other therapeutic ingredients.

The term "pharmaceutically acceptable salt" refers to salts prepared from pharmaceutically acceptable non-toxic acids or bases including inorganic acids and bases and organic acids and bases. Since the compounds of the present invention are acidic, salts may be prepared from pharmaceutically acceptable non-toxic bases including inorganic and organic bases. Suitable pharmaceutically acceptable base addition salts for the compounds of the present invention include metallic salts such as those made from aluminum, calcium, lithium, magnesium, potassium, sodium and zinc, or organic salts made from N,N'-dibenzylethylenediamine, chloroprocaine, choline, lysine, diethanolamine, ethylenediamine, meglumine (N-methylglucamine), procaine, and the like.

The compositions of the present invention include compositions such as suspensions, solutions, elixirs, and aerosols. Carriers such as starches, sugars, microcrystalline cellulose, diluents, granulating agents, lubricants, binders, disintegrating agents and the like may be used in the case of oral solid preparations. Oral solid preparations (such as powders, capsules, and tablets) are preferred over the oral liquid preparations. The most preferred oral solid preparation is tablets. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; and 4,008,719, the disclosures of which are hereby incorporated by reference.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent.

The invention is further defined by reference to the following examples describing in detail the compositions of the present invention as well as their utility. It will be apparent to those skilled in the art that many modifications, both to materials and methods, may be practiced without departing from the purpose and interest of this invention.

EXAMPLES 4.1. Example 1

The phenylquinone writhing test is a standard procedure for detecting and comparing analgesic activity in laboratory animals, and generally correlates well with human efficacy. In response to an injected, locally irritating solution, the animals have cramps ("writhings") that are inhibited by analgesic agents.

Mice are first dosed with at least two dose levels each of R(−) etodolac, S(+) etodolac, and racemic etodolac. The mice are then challenged with a solution of phenyl-p-benzoquinone given intraperitoneally and observed for the characteristic stretch-writhing syndrome. Lack of writhing is indicative of analgesic activity. The degree of analgesic activity is calculated on the basis of suppression of writhing relative to control animals tested the same day. Time response data are obtained by challenging the mice with the phenylquinone solution at different time intervals after dosing them with the test medications.

In this test, R(−) etodolac is found to be an effective analgesic.

4.2. Example 2

Toxicity

The following is a description of a study of the effects of the isomers of etodolac in the guinea pig. Groups of 6–10 guinea pigs are dosed orally with either vehicle, racemic etodolac (20, 10, 5, 1 and 0.1 mg/kg), S(+) etodolac (20, 10, 5, 1 and 0.1 mg/kg), or R(−) etodolac (20, 10, 5, 1 and 0.1 mg/kg). Within 24 hours after the dose, the animals are euthanized and gross abnormalities are recorded in the GI tracts, with particular attention to the gastric mucosa of the stomach. Microerosions and redness (irritations) are noted, and the effects are compared between the treatment groups as described by Aberg & Larsson, *Acta Pharmacol. Toxicol.* 28: 249–257 (1970). Based on such observations, the R(−) isomer is seen to cause virtually no gastrointestinal irritation.

4.3. Example 3

Leukopenia

To test white-cell survival, an in vitro test method is used, where a primary bone marrow cell culture is exposed to increasing concentrations of test compounds such as R(−) etodolac, S(+) etodolac, and racemic etodolac. A known inducer of leukopenia, such as thiouracil, is used as a positive control. The survival of the granulocyte is measured using conventional differential cell-counting methodology.

The risk for leukopenic effects of escalating concentrations of drugs in vivo is studied in groups of animals in which a mild granulocytopenia has initially been induced either by drugs such as thiouracil or chloramphenicol, or by radiation. Repeated white-cell counts are performed to monitor the development of leukopenia in the animals.

4.4. Example 4

Inhibitory Effect on the Activity of Cyclooxygenase

It is well-known that cyclooxygenase inhibitors (for example aspirin and indomethacin) cause damage and irritation of the gastric mucosa.

Assays to determine the inhibitory effect of R(–), S(+), and racemic etodolac, reference agents and vehicles on cyclooxygenase activity are conducted using RBL-1 cells (rat basophilic leukemia cell line). The effects of the test compounds, reference agents or vehicles are assessed on the cyclooxygenase-mediated production of $PGF_{2-alpha}$.

RBL-1 cells are grown in culture in Eagles's minimum essential medium supplemented with 12% fetal bovine serum and 1:100 antibiotic/antimycotic mixture at 37° C. Cells are harvested via centrifugation, washed with cold phosphate buffered saline (PBS), and suspended in PBS supplemented with 0.88 μM $CaCl_2$. Cells are incubated in the presence of a screening concentration of test compound or reference agent. Alternatively, cells are incubated in the presence of vehicle.

Following the incubation period, cyclooxygenase activity is stimulated by the addition of 5 μM of a calcium ionophore to the incubation medium. The reaction is terminated by chilling the tubes on ice.

The cells are then separated via centrifugation, and the supernatant is removed. Aliquots of the supernatant are used to measure the calcium-ionophore-stimulated production of $PGF_{2-alpha}$ via radioimmunoassay.

For each experiment, a vehicle-control is evaluated. A reference standard is also evaluated at a single concentration with each assay.

4.5. Example 5

| Capsules: | Oral Formulation | | |
|---|---|---|---|
| | Quantity per capsule in mg | | |
| Formula | A | B | C |
| Active ingredient | | | |
| R(–) Etodolac | 100.0 | 200.0 | 300.0 |
| Lactose | 148.5 | 248.5 | 148.5 |
| Titanium Dioxide | 0.5 | 0.5 | 0.5 |
| Magnesium Stearate | 1.0 | 1.0 | 1.0 |
| Compression Weight | 250.0 | 450.0 | 450.0 |

The active ingredient, R(–) etodolac, is sieved and blended with the excipients. The mixture is filled into suitable sized two-piece hard gelatin capsules using suitable machinery. Other doses may be prepared by altering the fill weight and if necessary, changing the capsule size to suit. Alternately, the active ingredients and suitable excipients may be prepared in the form of scored tablets.

What is claimed is:

1. A method of eliciting an analgesic effect in a human which comprises administering to a human in need of analgesic therapy, an amount of R(–) etodolac or a pharmaceutically acceptable salt thereof, substantially free of its S(+) stereoisomer, said amount being sufficient to alleviate pain.

2. A method of eliciting an analgesic effect in a human while substantially reducing the concomitant liability of adverse effects associated with the administration of racemic etodolac, which comprises administering to a human, in need of analgesic therapy, an amount of R(–) etodolac, or a pharmaceutically acceptable salt thereof, substantially free of the S(+) stereoisomer, said amount being sufficient to alleviate pain but insufficient to cause said adverse effects associated with the administration of the racemic mixture of etodolac.

3. The method of claim 1 wherein R(–) etodolac is administered by intrathecal or intravenous infusion, transdermal delivery, or orally as a tablet or a capsule.

4. The method of claim 3 wherein the amount of R(–) etodolac or a pharmaceutically acceptable salt thereof administered is from about 200 mg to about 2500 mg per day.

5. The method of claim 4 wherein the amount administered is from about 200 mg to about 1000 mg per day.

6. The method of claim 1 wherein the amount of R(–) etodolac or a pharmaceutically acceptable salt thereof is greater than approximately 90% by weight of the total weight of etodolac.

7. The method of claim 1 wherein the amount of said R(–) etodolac or a pharmaceutically acceptable salt thereof, substantially free of the S(+) stereoisomer, is administered together with a pharmaceutically acceptable carrier.

8. The method of claim 1 wherein R(–) etodolac is administered as a salt selected from the group consisting of sodium, calcium and lysinate salts.

9. A method of treating or preventing pyrexia in a human which comprises administering to a human an amount of R(–) etodolac or a pharmaceutically acceptable salt thereof, substantially free of its S(+) stereoisomer, said amount being sufficient to alleviate or prevent said pyrexia.

10. A method of treating or preventing pyrexia in a human, while substantially reducing the concomitant liability of adverse effects associated with the administration of racemic etodolac, which comprises administering to a human an amount of R(–) etodolac or a pharmaceutically acceptable salt thereof, substantially free of the S(+) stereoisomer, said amount being sufficient to alleviate or prevent said pyrexia but insufficient to cause said adverse effects associated with the administration of the racemic mixture of etodolac.

11. The method of claim 9 wherein R(–) etodolac is administered by intrathecal or intravenous infusion, transdermal delivery, or orally as a tablet or a capsule.

12. The method of claim 11 wherein the amount of R(–) etodolac administered is from about 200 mg to about 2500 mg per day.

13. The method of claim 12 wherein the amount administered is from about 200 mg to about 1000 mg per day.

14. The method of claim 9 wherein the amount of R(–) etodolac or a pharmaceutically acceptable salt thereof, is greater than approximately 90% by weight of the total weight of etodolac.

15. The method of claim 9 wherein the amount of R(–) etodolac or a pharmaceutically acceptable salt thereof, substantially free of the S(+) stereoisomer, is administered together with a pharmaceutically acceptable carrier.

16. The method according to claim 9 wherein R(–) etodolac is administered as a salt selected from the group consisting of sodium, calcium and lysinate salts.

* * * * *